United States Patent [19]

Calderó Ges et al.

[11] Patent Number: 5,331,005
[45] Date of Patent: Jul. 19, 1994

[54] AMIDINES DERIVED FROM 3-AMINOETHYL INDOLES AND PROCESS FOR THE PREPARATION THEREOF

[75] Inventors: José M. Calderó Ges; Anna Bosch Rovira; Joan Maria Roca Acin, all of Barcelona; Pere Dalmases Barjoan, Sant Feliu de Llobregat; Francisco Marquillas Olondriz, Barcelona, all of Spain

[73] Assignee: Vita-Invest, S.A., Sant Joan Despi, Spain

[21] Appl. No.: 87,004

[22] Filed: Jul. 7, 1993

[30] Foreign Application Priority Data

Jul. 20, 1992 [ES] Spain .................... 9201513

[51] Int. Cl.$^5$ .................... A61K 31/40; A61K 31/44; C07D 209/08; C07D 213/06
[52] U.S. Cl. .................... 514/415; 514/339; 548/505; 546/273
[58] Field of Search ............... 548/505; 514/415, 339; 546/273

[56] References Cited

U.S. PATENT DOCUMENTS 4,816,470  3/1989  Dowle et al. .................... 548/505
4,994,483  2/1991  Oxford et al. .................... 548/505

Primary Examiner—Robert W. Ramsuer
Assistant Examiner—Joseph K. McKane
Attorney, Agent, or Firm—Sughrue, Mion, Zinn, Macpeak & Seas

[57] ABSTRACT

Amidines derived from 3-aminoethyl indoles of formula (I)

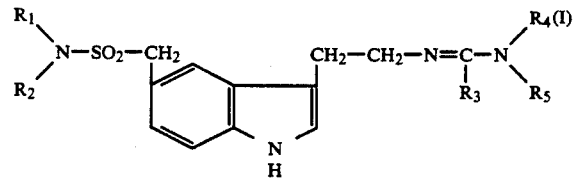

where $R_1$ is an atom of hydrogen or a lower alkyl or alkenyl group: $R_2$ is an atom of hydrogen or a lower alkyl or alkenyl, aryl, arylalkyl or cycloalkyl group; $R_3$ and $R_4$ may be the same or different and are an atom of hydrogen or a lower straight or branched chain alkyl group; and $R_5$ is an atom of hydrogen; a straight or branched chain alkyl, alkenyl or alkynyl group, which may be substituted with an hydroxy group, alkoxy, alkoxycarbonyl, carboxyl, trifluoromethyl, halogen, carbonyl, cyano; a cyano group, phenyl, aryl, cycloalkyl, heterocycle or arylalkyl, optionally substituted with a hydroxy, alkoxy, halogen, amino, alkoxycarbonyl, carboxyl, trifluoromethyl, carbonyl, cyano, nitro, lower alkyl, lower alkenyl, or may form an optionally substituted heterocycle with $R_4$ and with the nitrogen atom; and the physiologically acceptable salts thereof.

6 Claims, No Drawings

AMIDINES DERIVED FROM 3-AMINOETHYL INDOLES AND PROCESS FOR THE PREPARATION THEREOF

SUMMARY OF THE INVENTION

The invention concerns new amidines derived from 3-aminoethyl indoles, useful in the treatment of migraine, and also the process for the preparation thereof.

Among other possible origins, the migraine pain is associated with an excessive dilatation of certain brain vessels. The antimigraine products of this invention have vasoconstrictive properties, favorable for this therapy.

There is a need for an effective safe drug for the treatment of migraine which may be used prophylactically or to relieve a headache which has already started. Furthermore, it is desirable that the drug may be administered by any conventional way of administration and be lacking in toxic effects.

BACKGROUND OF THE INVENTION

A large number of indole derivatives having activity in the treatment of migraine have been described. Thus, Spanish patent application ES-523 039 discloses indoles of the general formula (II):

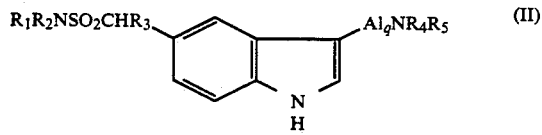

where $R_1$ is an atom of hydrogen or a $C_{1-6}$ alkyl group or a $C_{3-6}$ alkenyl group; $R_2$ is an atom of hydrogen or a $C_{1-3}$ alkyl, $C_{3-6}$ alkenyl, aryl, arylalkyl($C_{1-4}$) or cycloalkyl($C_{5-7}$) group; $R_3$ is an atom of hydrogen or a $C_{1-3}$ alkyl group; $R_4$ and $R_5$, which may be the same or different, are each an atom of hydrogen or a $C_{1-3}$ alkyl gropu or propenyl; or $R_4$ and $R_5$ together form an aralkylidene group: and Alk is an alkylene chain having two or three carbon atoms, which may be substituted or unsubstituted, by no more than two $C_{1-3}$ alkyl groups; and the physiologically acceptable salts and solvates thereof.

As disclosed in the aforesaid application ES-523 039, the compounds of the above formula have a vasoconstrictive action on the dog isolated vena saphena, rabbit isolated vena saphena preparation and on the carotid arterial circulation in the anaesthetized dog and therefore are potentially useful for the treatment of migraine.

In a later patent application ES-552 047 there is specifically selected and described within the field of the group of compounds described and claimed in Spanish patent application 523 039, a particular compound having special advantages in the treatment of migraine. This compound is 3-[2-(dimethylamino)ethyl)]-N-methyl-1H-indole-5-methane sulphonamide of formula (III).

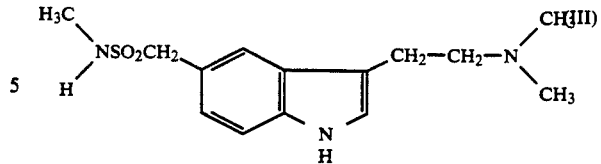

This formula (III) compound potently and selectively constricts the carotid arterial circulation after intravenous administration, as shown in experiments on anaesthetized dogs. A potent, selective vasoconstrictive action has also been shown in vitro. Tests on anaesthetized dogs have shown that the formula (III) compound is effectively absorbed consistently well in the gastrointestinal tract after intraduodenal administration, quickly producing a sustained vasoconstriction in the carotid arterial circulation.

DESCRIPTION OF THE INVENTION

The present invention provides some new compounds, 3-aminoethyl indole derivative amidines, of formula (I) and the physiologically acceptable salts thereof:

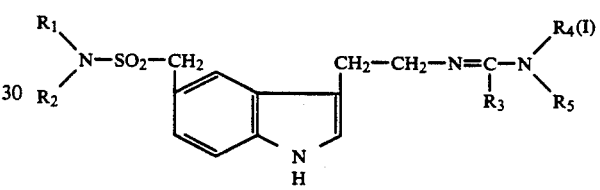

where $R_1$ is an atom of hydrogen or a lower alkyl or alkenyl group; $R_2$ is an atom of hydrogen or a lower alkyl or alkenyl group, an aryl, arylalkyl or cycloalkyl group; $R_3$ and $R_4$ may be the same or different and are an atom of hydrogen or a lower straight or branched chain alkyl; and $R_5$ is an atom of hydrogen; a straight or branched chain alkyl, alkenyl or alkynyl group, which may be substituted with a hydroxy group, alkoxy, alkoxycarbonyl, carboxyl, trifluoromethyl, halogen, carbonyl, cyano; a cyano group, phenyl, aryl, cycloalkyl, heterocycle or arylalkyl, optionally substituted with a hydroxy, alkoxy, halogen, amino, alkoxycarbonyl, carboxyl, trifluoromethyl, carbonyl, cyano, nitro, lower alkyl, lower alkenyl, or may form an optionally substituted heterocycle with $R_4$ and with the nitrogen atom.

As said above, these products are potentially useful for the prevention and treatment of migraine.

The in vitro tests carried out with the formula (I) compounds show a potent, selective vasoconstrictive action, It has also been observed that these products, when used at the dose levels effective for the treatment of migraine, have no significant effects on the blood pressure and the heart rate. The formula (I) compounds may be administered both orally and parenterally.

The appropriate physiologically acceptable salts of the formula (I) compounds include the acid addition salts formed with inorganic and organic acids, for example, hydrochlorides, hydrobromides, sulphates, nitrates, phosphates, formates, mesylates, citrates, benzoates, fumarates, maleates and succinates. When a salt of a formula (I) compound is formed with a dicarboxylic acid, such as succinic acid, the salt may contain one or two moles of the formula (I) compound per mole of acid. A preferred salt of the invention is the succinate, more preferably the 1:1 succinate.

The object of this invention allows the preventive or curative treatment of migraine in human beings by administration, through any conventional route, of a formula (I) compound or a physiologically acceptable salt or solvate thereof.

In accordance therewith, the invention also provides a pharmaceutical composition adapted for use in medicine, which comprises the formulation of a formula (I) compound and/or a physiologically acceptable salt or solvate thereof for oral, sublingual, parenteral, rectal or intranasal administration or in a form appropriate for administration by inhalation or insufflation.

The pharmaceutical compositions for oral administration may be solids, such as for example tablets or capsules prepared by conventional means with pharmaceutically acceptable excipients, or liquids, such as for example aqueous or oil solutions, syrups, elixirs, emulsions or suspensions prepared by conventional means with pharmaceutically acceptable additives.

The compounds of the invention may be administered, if desired, in combination with one or more different therapeutical agents, such as analgesics, antiinflammatory agents and antinausea agents.

The formula (I) compounds and the physiologically acceptable salts and solvates thereof, may be prepared by the general methods disclosed hereinafter.

(A) by reaction of an amine of formula (IV) with a reactive derivative of a carboxamide of formula (V)

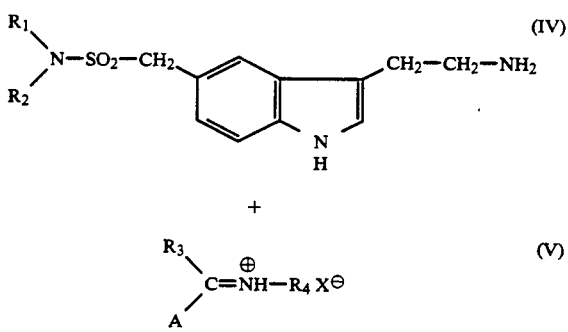

where:

$R_1$, $R_2$, $R_3$ and $R_4$ are as hereinbefore defined; and $X^-$ is an inorganic acid anion, such as chloride or fluoroborate; and A is a benzoyloxy group, chlorine, or lower alkoxy group, such as methoxy or ethoxy.

(B) or by reacting N-(indolylethyl)imidates of formula (IX)

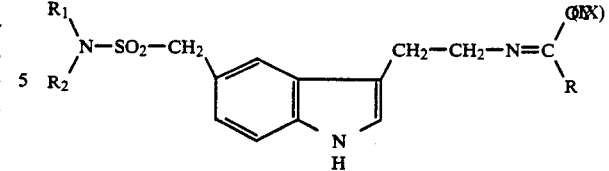

ps (where: $R_1$, $R_2$ and $R_3$ are as hereinbefore defined; and Y is a lower alkyl group, such as methyl or ethyl) with an amine of formula (X)

where: $R_4$ and $R_5$ are as hereinbefore defined.

(C) or by reacting carboxamide dialkylacetals of formula (XII)

(where $R_3$, $R_4$, $R_5$ and Y are as hereinbefore defined with an amine of formula (IV).

(D) or by reacting N,N'-disubstituted amidines of formula (XIII)

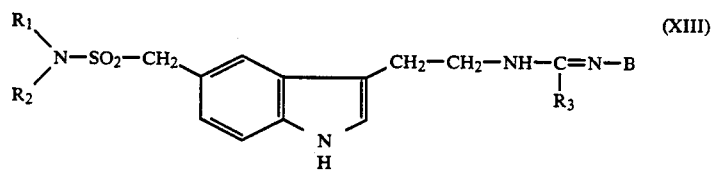

(where: $R_1$, $R_2$ and $R_3$ are as hereinbefore defined; and B is a cyano group, acetyl, carbethoxy or carbamoyl) with amines of formula (X).

In accordance with the general process (A), as stated hereinbefore, the formula (I) compounds may be prepared by reacting the formula (IV) amine with a reactive derivative of a formula (V) carboxamide.

If desired, the formula (V) compound may also be reacted in base form. The reaction is conducted at temperatures ranging from 0° to 100° C., preferably from 20° to 60° C. he reaction is advantageously conducted in an inert organic solvent such as for example alcohols, halogenated hydrocarbons, dioxane or acetone.

The starting formula (IV) amine may be prepared following the process disclosed in ES-523 039 by cyclization of the corresponding hydrazone to indole by the known Fisher indolization reaction (The Fisher—Indole Synthesis, B. Robinson p488—Wiley 1982). Alternatively the formula (IV) amine may be prepared by decarboxylation of the corresponding amino acid of formula (VI).

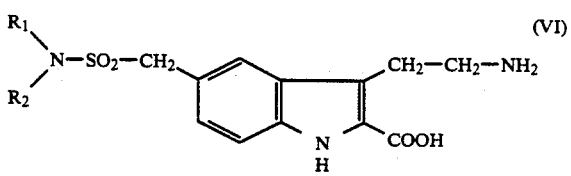

Alternatively, the formula (IV) amine may also be prepared by reduction of the corresponding nitroethylene derivative of formula (VII).

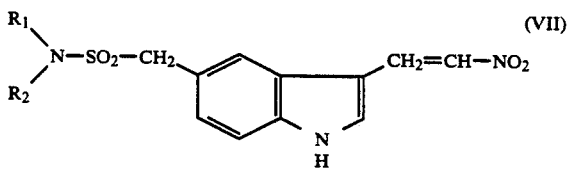

The formula (V) compounds, used as starting reactants in the above process (A), may be prepared by the conventional methods, by reacting a carboxamide of formula (VIII)

where $R_3$ and $R_4$ are as hereinbefore defined, with benzoyl chloride, triethyl oxonium fluoroborate, ethyl chloroformate, phosphorus oxychloride or phosphorus pentachloride.

In accordance with another general process (B) and also in accordance with what has been said above, the general formula (I) compounds may be prepared from N-(indolylethyl) imidates of formula (IX) with an amine of formula (X).

This reaction is advantageously conducted in an inert organic solvent such as methanol, ethanol or dioxane.

The reaction may also be conducted in the absence of a solvent, or using an excess of the formula (X) amine as solvent. The reaction is conducted at a temperature ranging from 20° to 80° C.

The general formula (IX) compounds, used as starting reactants, may be prepared by methods known in the literature, such as, for example, by reacting a formula (IV) amine with a compound of formula (XI)

in the absence of a solvent and removing the alcohol formed during the reaction by distillation.

If desired, the process may be carried out in a single synthesis step, by reacting formula (IV) amines with a formula (XI) compound, $R_3$ and Y having the meaning given hereinbefore, in the presence of an inorganic acid, such as for example sulphuric acid, as catalyst. The reaction is conducted at a temperature ranging from 60° to 120° C. After a few hours, the appropriate formula (X) amine is added to the reaction mixture.

Also according to the foregoing, in an alternative process (C), carboxamide dialkylacetals of formula (XII) are reacted with formula (IV) amines to give the compounds of the general formula (I). The reaction is conducted at temperatures ranging from 20° to 80° C., with the alcohol formed during the reaction being removed by distillation.

Finally, in accordance with a further alternative process (D), to which reference has already been made, N,N'-disubstituted amidines of formula (XIII) are reacted with formula (X) amines to give the products of the general formula (I).

This reaction is suitably conducted in the presence of water or an inert organic solvent, such as alcohol, formamide, dioxane or acetonitrile.

This reaction may be conducted at temperatures ranging from 10° to 50° C., preferably at room temperature.

The formula (XIII) compounds used as starting products in the foregoing process (D) are prepared by known-methods, for example, by reaction of a formula (IV) amine with an N-substituted ethyl imidate of formula (XIV)

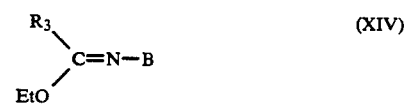

where $R_3$ and B are as hereinbefore defined. Optionally, where in the formula (XIV) compound, B is a cyano group, the reaction may also be conducted in a single step, by reacting the formula (IV) amine with cyanamide, in the presence of a formula (XI) compound, where Y and $R_3$ have the meaning given hereinbefore.

The process D) reaction is conducted in the presence of an appropriate inert organic solvent such as, for example, alcohol, ether, ethyl acetate, acetonitrile or dioxane or without solvent, at temperatures ranging from 20° to 80° C.

The compound of the general formula (XIV) may be prepared by conventional methods.

The following test was conducted to evaluate the pharmacological activity of the synthesized products:

5HT$_1$-like antagonist activity of the synthesis products on isolated dog vena saphena preparation.

The method described by Humphrey et El, Br. J. Pharmacol., 94/4, 1123–1132 (1988) was followed. Here a portion of vena saphena was taken from dogs sacrificed with an overdose of sodium pentobarbital, and was prepared as described by Apperly et El., Br. J. Pharmacol., 58, 211–221 (1976). The vascular rings were mounted in an organ bath with Krebs-Henseleit at 37° C., aerated with a 95% 0.5 and CO$_2$ gas mix Each ring was subjected to a stress of 0.5 g, being allowed to rest for 60 rain with the stress being readjusted periodically. The maximum contracting response was obtained at a concentration of 30 mM KCl. Cumulative concentration-response curves were drawn up for each antagonist studied and the pD$_2$ values were calculated to characterize the potency of each of the products being studied.

| Product | pD$_2$ |
| --- | --- |
| 1 | 5.1 |
| 2 | 6.2 |
| 3 | 5.3 |
| 4 | 5.6 |
| Sumatriptan succinate | 6.2 |

EXPERIMENTAL

The following preparations are given as an example to illustrate the invention.

EXAMPLE 1

3-[2-(N,N-dimethylaminomethyleneamino)ethyl]-1H-indole-5-yl-N-methyl methane sulphonamide. 1

5 g (0.01873 m) of 3-(2-aminoethyl)-1H-indole-5-yl-N-methyl methane sulphonamide in 300 mL of toluene were charged in a 500 mL round bottom flask, with nitrogen flow. 5.12 mL (0.03745 m) of dimethylformamide dimethylacetal were added and the mixture was stirred at room temperature for three days. When the reaction was deemed to have terminated, as per the TLC control (eluant: butanol/acetic acid/$H_2O$ 65/13/22) the insoluble solid was filtered, was washed with 50 mL of toluene and dried in a current of air at 50° C. 5.6 g of 3-[2(N, N-dimethylaminomethyleneamino)ethyl]-1H-indole-5-yl-N-methyl methane sulphonamide were obtained, in the form of a creamy white colored solid, representing a 93% yield. M.p.=174°-175° C.

IR(KBr disc): 3255, 2830, 1644, 1305, 1105 cm$^{-1}$, $H^1$-NMR d$_6$-DHSO): 2. 55 (broad signal (3H) CH$_3$NHSO$_2$), 2.76 (s, (6H)N(CH$_3$)$_2$ ), 2. 81 (t(2H)CH$_2$CH$_2$N), 3.4 (t(2H) CH$_2$CH$_2$N), 4. 2 (s(2H) NHSO$_2$CH$_2$), 6.8 (m (1H) NHSO$_2$, D$_2$O exch.), 7.8(d×d (1H) Ar), 7.14 (d (1H) Ar), 7.32 (d (1H) Ar), 7.36 (s (1H) N=CH—N), 7.55 (d (1H) At), 10.8 (s (1H) NH indole, D$_2$O exch. )

Elementary analysis: C$_{15}$H$_{22}$N$_4$SO$_2$ (MW=322.425)
% Calculated: C: 55.88 H: 6.88 N: 17.38 S: 9.94; Found: C: 55.45 H: 6.92 N: 17.12 S: 9.82.

EXAMPLE 2

3-[2-(N,N-diethylaminomethyleneamino)ethyl]-1H-indole-5-yl-N-methyl methane sulphonamide. 2

5 g (0,01873 m) of 3-(2-aminoethyl)-1H-indole-5-yl-N-methyl methane sulphonamide in 300 mL of toluene were charged in a 500 mL round bottom flask, with nitrogen flow. 5.51 g (0.03745 m) of dimethylformamide diethylacetal (H. Bredereck, Chem. Bet., 101, 41 (1968)) were added and the mixture was stirred at room temperature for two days. When the reaction was deemed to have terminated, as per the TLC control (eluant: butanol/acetic acid/$H_2O$ 65/13/22) the insoluble solid was filtered, was washed with 50 mL of toluene and dried in a current of air at 50° C. 5.3 g of 3-[2-(N,N-diethylaminomethyleneamino)ethyl]-1H-indole-5-yl-N-methyl methane sulphonamide were obtained, in the form of a creamy white colored solid, representing a 81% yield. M.p.=98°-99° C.

IR (KBr disc): 3255, 2830, 1645, 1305, 1115 cm$^{-1}$
$H^1$-NMR (d$_6$-DMSO).

1 (t(6H) CH$_3$CH$_2$), 2.55 (broad signal (3H) CH$_3$NHSO$_2$), 2.8 (t(2H) CH$_2$CH$_2$N), 3.18 (c(4H) CH$_2$ CH$_3$) 3.4 (t(2H) CH$_2$CH$_2$N), 4.18 (s(2H) NHSO$_2$CH$_2$), 6.8 (m(1H)NH SO$_2$, D$_2$O exch. , 7.1 (d×d (1H) Ar), 7.15 (d(1H)Ar), 7.35 (d(1H)Ar), 7.37 (s(1H) N=CH—N), 7.55 (s(1H)AF), 10.8 (s(1H)NH indole, D$_2$O exch. ).

Elementary analysis: C$_{17}$H$_{26}$N$_4$SO$_2$ (MW=350.478).
% Calculated: C: 58.26 H: 7.48 N: 15.99 S: 9.13; % Found: C: 58.37 H: 7.32 N: 15.72 S: 9.25.

EXAMPLE 3

3-[2-(N,N-dipropyaminomethyleneamino)ethyl]-1H-indole-5-yl-N-methyl methane sulphonamide. 3

The same method as in the previous Example was followed, starting from 0.5 g (0.001873 m) of 3-(2-aminoethyl)-1H-indole-5-yl-N-methyl methane sulphonamide and 0.6 g (0.003745 m) of dimethylformamide dipropylacetal (H. Brederick, Chem, Bet., 101, 41 (1968)). 0.45 g of 3-[2-(N,N-dipropylaminomethyleneamino)ethyl]-1H-indole-5-yl-N-methyl methane sulphonamide were obtained, in the form of an oil, representing an 84.7% yield.

IR(KBr disc): 3200, 2950, 1645, 1450, 1305, 1115 cm$^{-1}$.

$H^1$-NMR (d$_6$-DMSO):

0.8 (1(6H)CH$_3$CH$_2$CH$_2$), 1.42 (m(4H)CH$_3$CH$_2$CH$_2$), 2.55 (broad signal (3H )CH$_3$NHSO$_2$), 2.82 (t(2H)CH$_2$CH$_2$N ), 3.2 (c(4H)CH$_2$CH$_2$N), 3.4 (c(4H)CH$_3$CH$_2$CH$_2$), 4.2 (s( 2H)NHSO$_2$CH$_2$, 6.8 (broad signal (1H)NHSO$_2$, D$_2$O exch.), 7.08 (d×d(1H)Ar), 7.15 (d(1H)Ar), 7.31 (d(1H)Ar), 7.4 (s(1H)N=CH—N), 7.55 (d(1H)Ar), 10.9 (s( 1H)NH indole, D$_2$O exch. )

Elementary analysis: C$_{19}$H$_{30}$N$_4$SO$_2$ (MW=378.532)
% Calculated: C: 60.30 H: 7.99 N: 14.80 S: 8.47; % Found: C: 59.98 H: 7.86 N: 14.72 S: 8.52.

EXAMPLE 4

3-[2-(N-phenylaminomethyleneamino)ethyl]-1H-indole-5-yl-N-methyl methane sulphonamide. 4

2.67 g (0.01 m) of 3-(2-aminoethyl)-1H-indole-5-yl-N-methyl methane sulphonamide and 10 mL of acetone were charged in a 25 mL round bottom flask. 1.64g (0.01 m) of ethyl N-phenylformimidate were added and the mixture was stirred at room temperature for 24 hours. When the reaction was deemed to have terminated, as per the TLC control (eluant: butanol/acetic acid/$H_2O$ 65/13/22) the acetone was concentrated to dryness and the oil obtained was crystallized from toluene. It was filtered, was washed with 10 mL of toluene and dried in a current of air at 50° C. to give 2.5 g of 3-[2-(N-phenylaminomethyleneamino)ethyl]-1H-indole-5-yl-N-methyl methane sulphonamide, in the form of a cream colored solid, representing a 67% yield. M.p.=72°-73° C.

IR (KBr): 3400, 2920, 1635, 1590, 1490, 1300, 1110 cm$^{-1}$.

$H^1$-NMR (d$_6$-DHSO ):

2.55 (broad signal (3H ) CH$_3$NHSO$_2$), 2.95 (t(2H )CH$_2$CH$_2$N), 3.58 (t(2H)CH$_2$CH$_2$N), 4.2 (s(2H)NHSO$_2$CH$_2$) 6.8 (m(1H)NHSO$_2$, D$_2$O exch. ), 6.8-7.8 (complex signal (9H) 8HAr+N=CH—N), 10.9 (s(1H)NH indole, D$_2$O exch.).

Elementary analysis: C$_{19}$H$_{22}$N$_4$O$_2$ (MW=370.469).
% Calculated: C: 61.60 H: 5.99 N: 15.12 S: 8.65; % Found: C: 61.72 H: 5.78 N: 15.03 S: 8.42 .

EXAMPLE 5

3-[2-{N-(3-pyridyl)aminomethyleneamino}ethyl]-1H-indole-5-yl-N-methyl methane sulphonamide. 5

2.67 g (0.01 m) of 3-(2-aminoethyl)-1H-indole-5-yl-N-methyl methane sulphonamide and 10 mL of acetone were charged in a 25 mL round bottom flask. 1.5 g (0.01 m) of N-(3-pyridyl)formiminoethyl ether (V. P. Benko, J. Prackt. Chem. 313, 179, (1971)) were added and the mixture was stirred at room temperature for 24 hours. When the reaction was deemed to have terminated, as per the TLC control (eluant: butanol/acetic acid/$H_2O$ 65/13/22) the acetone was concentrated to dryness and the oil obtained was crystallized from toluene. It was filtered, was washed with 10 mL of toluene and dried in a current of air at 50° C. to give 2.7 g of 3-[2-{N-(3-pyridyl)aminomethyleneamino}ethyl]-1H-indole-5-yl-N-methyl methane sulphonamide, in the form of a cream colored solid, representing a 73% yield. M.p.=70°-71° C.

IR (KBr): 3400, 2920, 1640, 1580, 1480, 1310, 1120, 810 cm$^{-1}$.

$H^1$-NMR (d$_6$-DMSO): 2.55 (broad signal (3H)$CH_2NHSO_2$), 3 (t(2H)$CH_2CH_2N$), 3.6 (t(2H)$CH_2CH_2N$), 4.2 (s(2H) $NHSO_2CH_2$), 6.8 (m(1H) $NHSO_2$, $D_2O$ exch.), 7-7.9 (complex signal (7H)$H_2$, $H_4$, $H_6$, $H_7$ of the benzimidazole and $H_4$, $H_5$ and $H_6$ of the pyridine), 8.1 (complex signal (1H)$H_2$ of the pyridine), 11 (s(1H) NH indole, $D_2O$ exch.)

Elementary analysis: $C_{18}H_{22}N_4SO_2$ (MW=371.46).

% Calculated: C: 58.20 H: 5.70 N: 18.85 S: 8.63; % Found: C: 58.06 H: 5.92 N: 18.63 S: 8.82.

EXAMPLE 6

3-[2-{N-(3-chlorophenyl)aminomethyleneamino}ethyl]-1H-indole-5-yl-N-methyl methane sulphonamide. 6

The same method as in the previous Example was followed, starting from 2.67 g (0.01 m) of 3-(2-aminoethyl)-1H-indole-5-yl-N-methyl methane sulphonamide and 1.84 g (0.01 m) of ethyl 3-chlorophenylformimidate. 2.8 g of 3-[2-{N-(3-chlorophenyl)aminomethyleneamino}ethyl]-1H-indole-5-yl-N-methyl methane sulphonamide were obtained, in the form of an oily solid, having an Rf of 0.75 in butanol/acetic acid/$H_2O$ 65/13/22.

IR(KBr): 3400, 2920, 1640, 1590, 1480, 1310 1120 cm$^{-1}$;

$H^1$-NMR (d$_6$-DMSO):

2.55 (broad signal (3H)$CH_3NHSO_2$), 3(t(2H)$CH_2CH_2N$), 3.6 (t(2H)$CH_2CH_2N$), 4.2 (s, (2H)$NHSO_2CH_2$) 6.8 (m(1H)$NHSO_2$, $D_2O$ exch. ), 6.9-7.8 (complex signal (8H) phenyl and benzimidazole hydrogens) 11(s (1H)NH indole, $D_2O$ exch.)

Elementary analysis: $C_{19}H_{21}ClN_4SO_2$ (MW=404.914)

% Calculated: C: 56.36 H: 5.23 Cl: 8.75 N: 13.84 S: 7.92; % Found: C: 56.21 H: 5.46 Cl: 8.62 N: 13.72 S: 8.02.

EXAMPLE 7

3-[2-[N-(3-chloro-2-methylphenyl)aminomethyleneamino]ethyl-1H-indole-5-yl-N-methyl methane sulphonamide. 7

The same method as in the previous Example was followed, starting from 2.67 9 (0.01 m) of 3-(2-aminoethyl)-1H-indole-5-yl-N-methyl methane sulphonamide and 1.97 9 (0.01 m) of ethyl 3-chloro-2-methylphenyl formimidate, 2.95 g of 3-[2-[N-(3-chloro-2-methylphenyl)aminomethyleneamino]ethyl]-1H-indole-5-yl-N-methyl methane sulphonamide were obtained, in the 3O form of a cream colored solid, representing a 70.4% yield. M.p.: 98°-99° C. IR (KBr): 3400, 2920, 1640, 1580, 1460, 1310, 1120 cm$^{-1}$ $H^1$ -NHR (d$_6$-DMSO):

2.4 (s(3H)$CH_3Ar$) 2.55 (broad signal (3H)$CH_3NHSO_2$), 3 (t(2H)$CH_2CH_2N$), 3.6 (t(2H)$CH_2CH_2N$), 4.2 (s(2H)$NHSO_2CH_2$) 6.8 (m(1H)$NHSO_2$, $D_2O$ exch.), 7-7.7 (complex signal (7H) 4 benzimidazole protons and 3 phenyl protons).

11 (s( 1H)NH indole, DO exch.),

Elementary analysis: $C_{20}H_{23}ClN_4SO_2$ (MW=418.941).

% Calculated: C: 57.34 H: 5.53 Cl: 8.46 N: 13.37 S: 7.65; % Found: C: 57.18 H: 5.62 Cl: 8.42 N: 13.12 S: 7.82.

EXAMPLE 8

3-[2-{N-(2,5-difluorophenyl)aminomethyleneamino}ethyl]-1H-indole-5-yl-N-methyl methane sulphonamide. 8

The same method as in the previous Example was followed, starting from 2.67 g (0.01 m) of 3-(2-aminoethyl)-1H-indole-5-yl-N-methyl methane sulphonamide and 2.8 g (0.01 m) of ethyl 2,5-difluorophenyl formimidate. 3.1 g of 3-[2-{N-(2,5-difluorophenyl)aminomethyleneamino}ethyl]-1H-indole-5-yl-N-methyl methane sulphonamide were obtained, in the form of a pasty solid, representing a 76% yield. This product; has an Rf of 0.7 in butanol/acetic acid/$H_2O$ 65/13/22.

IR (KBr): 3400, 2920, 1640, 1600, 1500, 1305, 1140, 1120 cm$^{-1}$.

$H^1$-NMR (d$_6$-DMSO): 2.5 (broad signal (3H)$CH_3NHSO_2$), 3 (t(2H)$CH_2CH_2N$) , 3.6 (t(2H)$CH_2CH_2N$), 4.2 (s(2H)$NHSO_2CH_2$), 6.8 (m(1H)$NHSO_2$, $D_2O$ exch. ), 7-7.8 (complex signal (7H) 4 benzimidazole protons and 3 phenyl protons), 10.95/s(1H) NH indole, $D_2O$ exch.).

Elementary analysis: $C_{19}H_{20}F_2N_4SO_2$ (MW=406.45).

% Calculated: C: 56.15 H: 4.96 F: 9.35 N: 13.78 S: 7.89; % Found: C: 56.02 H: 4.83 F: 9.42 N: 13.83 S: 7.74.

What we claim is:

1. An amidine of formula (I)

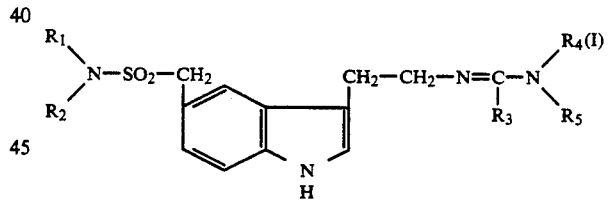

where:

R$_1$ is an atom of hydrogen or a lower alkyl or alkenyl group:

R$_2$ is an atom of hydrogen or a lower alkyl or alkenyl group, aryl, arylalkyl or cycloalkyl group;

R$_3$ and R$_4$ may be the same or different and are an atom of hydrogen or a lower straight or branched chain alkyl group; and R$_5$ is an atom of hydrogen; a straight or branched chain alkyl, alkenyl or alkynyl group, which may be substituted with an hydroxy group, alkoxy, alkoxycarbonyl, carboxyl, trifluoromethyl, halogen, carbonyl cyano; a cyano group, phenyl, aryl, cycloalkyl, heterocycle or arylalkyl, optionally substituted with a hydroxy group, alkoxy, halogen, amino, alkoxycarbonyl, carboxyl, trifluoromethyl, carbonyl, cyano, nitro, lower alkyl or lower alkenyl, or may form an optionally substituted heterocycle with R$_4$ and with the nitrogen atom; and the physiologically acceptable salts thereof.

2. The amidine of claim 1, wherein is methyl and $R_2$, $R_3$ and $R_4$ are hydrogen.

3. The amidine of claim 1 or 2, wherein $R_5$ is phenyl optionally substituted with hydroxy, alkoxy, halogen, amino, alkoxycarbonyl, carboxyl, trifluoromethyl, carbonyl, cyano, nitro, lower alkyl or lower alkenyl.

4. 3-[2-{N-phenylamino(methyleneamino)ethyl}]-1H-indole-5-yl-N-methyl methane sulphonamide or a pharmaceutically acceptable salt thereof.

5. A pharmaceutical composition comprising an amidine of any one of claims 1, 2 or 4, in an amount effective for treating migraine in combination with at least one pharmaceutical support, diluent or excipient.

6. A method for treatment of migraine which comprises administering a migraine treatment effective amount of a compound of any of claims 1, 2 or 4, to a patient in need of such treatment.

* * * * *